(12) United States Patent
Wang

(10) Patent No.: US 7,408,162 B2
(45) Date of Patent: Aug. 5, 2008

(54) METHOD FOR REDUCING NUCLEAR MEDICINE SCANNING TIME

(75) Inventor: Sharon Xiaorong Wang, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/239,271

(22) Filed: Sep. 29, 2005

(65) Prior Publication Data

US 2007/0069138 A1    Mar. 29, 2007

(51) Int. Cl.
*G01T 1/166*    (2006.01)

(52) U.S. Cl. .................................................. 250/363.04

(58) Field of Classification Search ............ 250/363.02, 250/363.04
See application file for complete search history.

(56) References Cited

U.S. PATENT DOCUMENTS

| | | | | |
|---|---|---|---|---|
| 4,503,331 A * | 3/1985 | Kovacs et al. | ........... | 250/363.04 |
| 5,444,252 A * | 8/1995 | Hug et al. | ............... | 250/363.08 |
| 5,677,535 A * | 10/1997 | Stephan | .................. | 250/363.02 |
| 5,691,538 A * | 11/1997 | Ohike et al. | ........... | 250/363.05 |
| 5,777,332 A * | 7/1998 | Lonn et al. | ............. | 250/363.04 |
| 5,811,813 A * | 9/1998 | Maor | ..................... | 250/363.05 |
| 5,838,009 A * | 11/1998 | Plummer et al. | ....... | 250/363.05 |
| 5,929,446 A * | 7/1999 | Plummer et al. | ....... | 250/363.05 |
| 6,147,353 A * | 11/2000 | Gagnon et al. | ......... | 250/363.05 |
| 6,204,503 B1 * | 3/2001 | Pierfitte et al. | ......... | 250/363.05 |
| 6,288,397 B1 * | 9/2001 | Maor | ..................... | 250/363.08 |
| 2004/0263865 A1 * | 12/2004 | Pawlak et al. | ................ | 356/622 |
| 2006/0000983 A1 * | 1/2006 | Charron et al. | ............. | 250/394 |

* cited by examiner

*Primary Examiner*—David P. Porta
*Assistant Examiner*—Marcus H Taningco
(74) *Attorney, Agent, or Firm*—Peter L. Kendall

(57) ABSTRACT

A method for reducing the scanning time of SPECT broadly includes determining a physical characteristic of an object within a radiation field, calculating an optimal starting angle of at least two detectors based on the physical characteristic of the object and a trajectory of the at least two detectors such that the geometric efficiency of the detectors along the trajectory can be maximized, angularly displacing the detectors based on the calculated optimal starting angle, scanning the object within the field to detect one or more gamma photons emanating from the object, and preparing an image from the one or more detected gamma photons. Preferably, the physical characteristic of the object is its location within the field, but can include properties such as signal to noise ratio, shape of the object, etc.

23 Claims, 5 Drawing Sheets

METHOD FOR REDUCING NUCLEAR MEDICINE SCANNING TIME

FIELD OF THE INVENTION

The present invention generally relates to nuclear medicine, and systems for obtaining nuclear medicine images. In particular, the present invention relates to a method for reducing the scanning time of Single Photon Emission Computed Tomography (SPECT).

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by scintillation crystals with which the photons interact to produce flashes of light or events. In SPECT, events are detected by one or more collimated gamma photon detectors, also referred to as gamma cameras, which are typically rotated about a patient's body. Using the experimental data that is collected, three-dimensional images of the organs of the body, which have been taken up the radiopharmaceuticals, e.g. the heart, can be constructed.

While SPECT is a powerful tool in the clinician's toolbox, it suffers from at least one drawback—SPECT imaging can be time consuming when compared with other types of imaging procedures. For example, whereas CT scanning procedures can take as little as a minute to complete, SPECT procedures can take more than fifteen minutes to complete. This is problematic because it can be difficult for a patient to remain still for such time periods, which can affect image quality. Similarly, some patients may be unwilling to undergo scanning procedures that take such long periods of time.

The amount of time that it takes to scan a patient using SPECT can be attributed to a number of factors. Most significantly, however, is the fact that SPECT detectors include collimating devices that only allow gamma photons traveling along precise trajectories to interact with the detectors. As a result, it can take time for a sufficient number of gamma photons to interact with the detectors to produce an image. Other factors that can affect SPECT scanning time include, but are not limited to, the distance between an object and a detector, the amount of tissue between an object and a detector, and angle of orientation of the SPECT detectors with respect to the object being studied. For example, many SPECT detectors are oriented at −45° starting angles and travel along elliptical trajectories centered about a patient's body. However, areas of interest, such as the human heart, are centrally located within the body. As a result, the distances, angles of orientation, and trajectory of the SPECT detectors are not optimized, or geometrically efficient, for performing such scans. Consequently, unnecessary time is expended when scanning such objects using these types of systems.

What is needed then is a method for optimizing a starting angle of a SPECT detector to maximize the geometrical efficiency of the detectors along a trajectory.

SUMMARY OF THE INVENTION

The present invention broadly comprises a method for acquiring images within a radiation field, preferably using a SPECT scanning system. The method broadly comprises determining a spatial location of an object within a radiation field, calculating an optimal starting angle of at least two detectors based on the spatial location of the object within the field such that the geometrical efficiency of the detectors along a trajectory can be maximized, angularly displacing the detectors based on the calculated optimal starting angle, scanning the object within the field to detect one or more gamma photons emanating from the object, and preparing an image from the one or more detected gamma photons.

More specifically, the present invention establishes an objective function that is the integral of the distance from an object, e.g., the heart of a patient, to a pair of detectors and optimizes it in the least square sense. The objective function accounts for the offset of the object, e.g., the heart, with respect to the detectors and optimizes the starting angle of the detectors based on the trajectory. Because the detectors are ultimately positioned closer to the object being scanned as a result of the modified starting angle, the geometric efficiency can be increased such that a same number of counts can be acquired in a shorter scan time period.

In some embodiments of the invention a SPECT scanning system includes a pair of detectors having an optimal starting angle that can be described by $D(\phi)=D_1^2(\phi)+D_2^2(\phi)$ and $$f(\alpha) = \int_\alpha^{\alpha+\theta°} D(\varphi)d\varphi,$$

wherein D corresponds to detector distance from the object, $\theta$ corresponds to the period of the detector trajectory, $\phi$ corresponds to detector rotation angle during scanning, $\alpha$ corresponds to detector starting angle, wherein $f(\alpha)$ achieves a minimum value.

In some embodiments and depending upon the configuration of the detectors, $\theta$ can describe any period, but in some instances describes periods of 90° or 180°. In some embodiments of the invention, each of the at least two detectors are disposed at a 90° angles with respect to one another. In some embodiments of the invention, each of the at least two detectors are disposed at 180° angles with respect to one another. In some embodiments of the invention, each of the at least two detectors are disposed at a 76° angles with respect to one another. In some embodiments of the invention, while the trajectory of the detectors can be any trajectory, e.g., an ellipse, a circle, an arc, a line, or a portion or combination thereof, in most instances the trajectory comprises an ellipse for accommodating the human body.

In some embodiments of the invention, the method includes determining a physical characteristic of an object within a radiation field, calculating an optimal starting angle of at least two detectors based on the physical characteristic of the object such that the geometric efficiency of the detectors along a trajectory can be maximized, angularly displacing the detectors based on the calculated optimal starting angle, scanning the object within the field to detect one or more gamma photons emanating from the object, and preparing an image from the one or more detected gamma photons. Preferably, the physical characteristic is spatial location of the object within the field, or distance from the object to the detectors, but can include other physical properties of the object and/or of the object within the field, e.g., signal to noise ratio, shape of the object, etc.

BRIEF DESCRIPTION OF THE DRAWINGS

The invention will now be more fully described by way of example with reference to the accompanying drawings in which.

Figure 2:
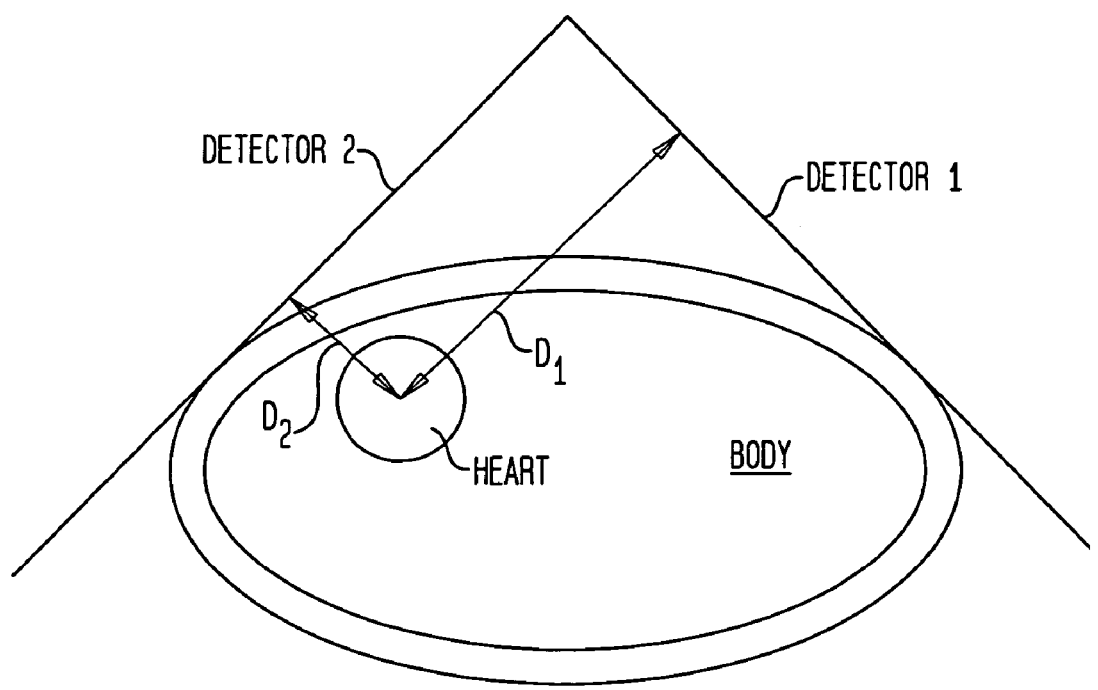
FIG. 2 is a schematic illustration of a known SPECT scanning system depicting detectors 1 and 2 disposed with respect to one another at an angle of 90° and at a −45° starting angle; detectors 1 and 2 are illustrated as being at distances $D_1$ and $D_2$ from the patient's heart.
Figure 3:
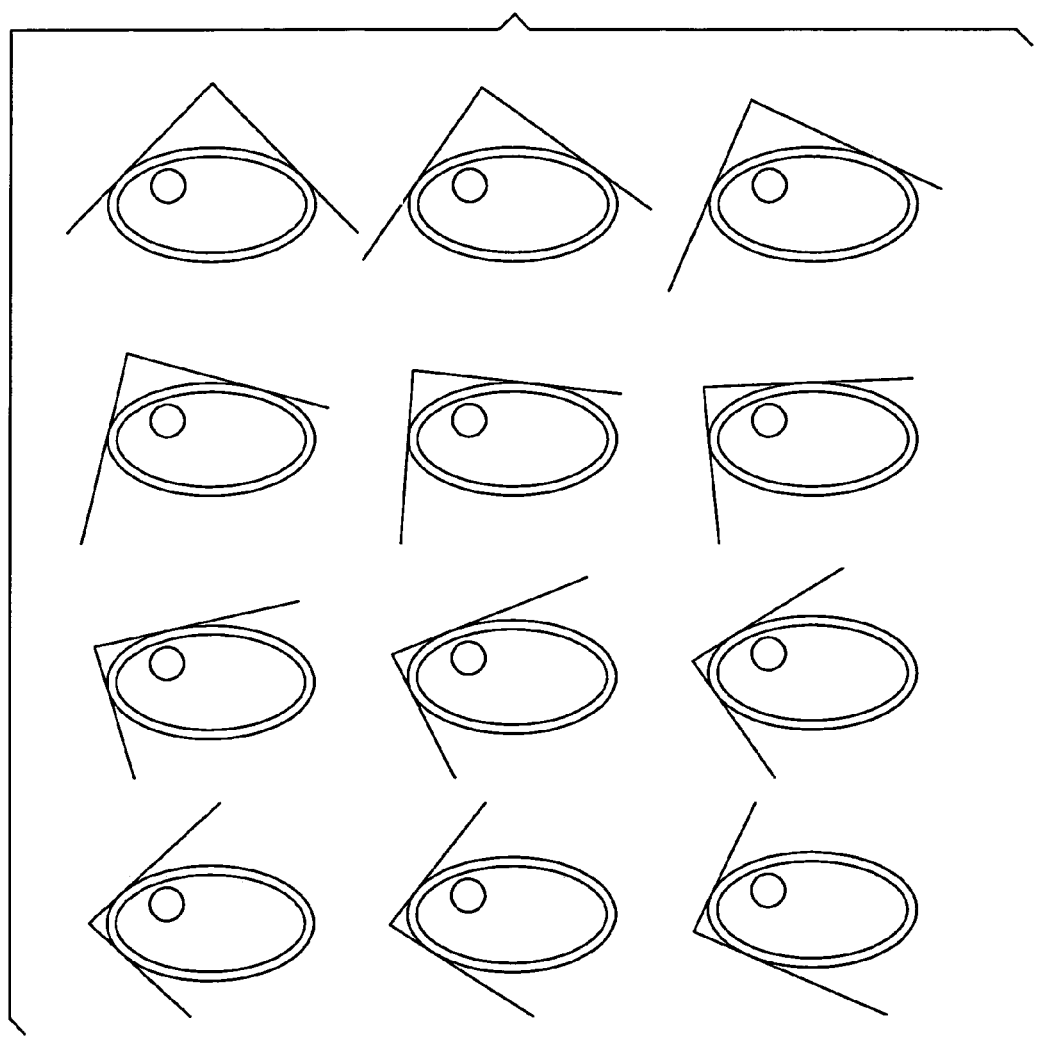
FIG. 3 is a schematic illustration depicting relative positions of detectors 1 and 2 of FIG. 2 during a typical SPECT scanning procedure along an elliptical trajectory.
Figure 6:
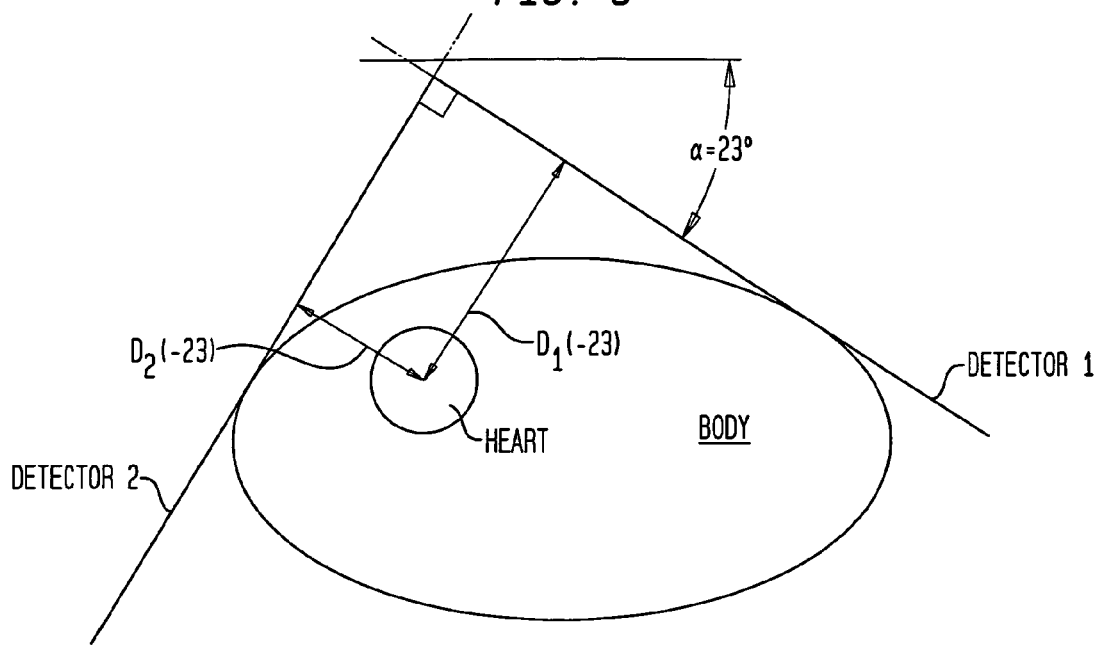
Figure 7:
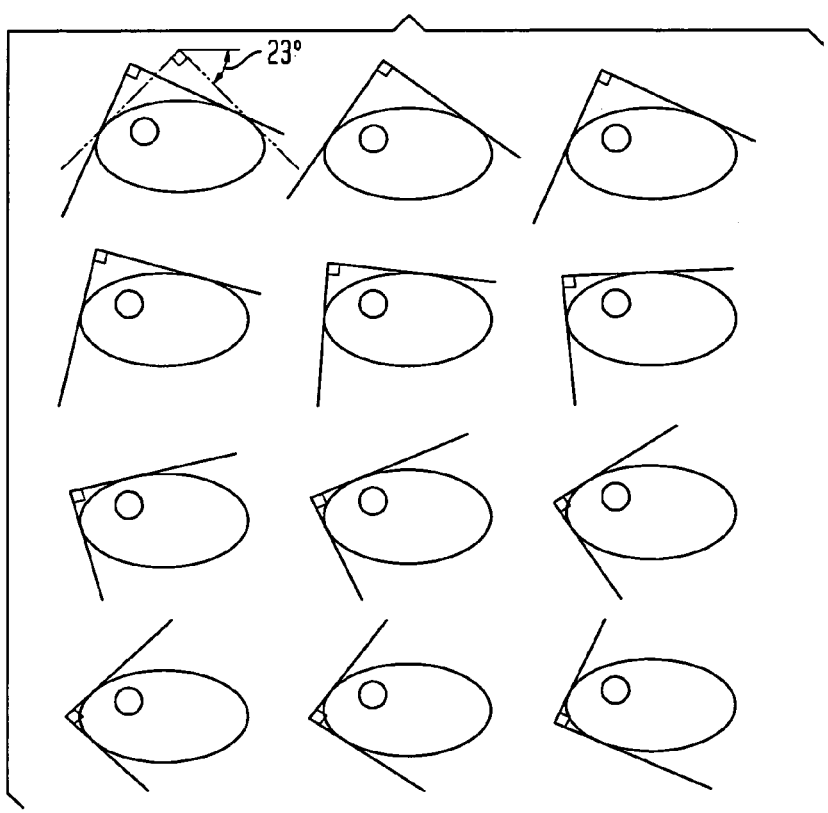

of the trajectory, the light vertical line indicates detector start angle at which the minimum of the objective function is achieved;

FIG. 6 is a schematic illustration of a SPECT scanning system similar to FIG. 2, but depicting detectors 1 and 2 disposed at an optimal starting angle according to the present invention; detectors 1 and 2 are illustrated as being at distances $D_1$ and $D_2$ from the patient's heart; and, FIG. 7 is schematic illustration, similar to FIG. 3, but depicting relative positions of detectors 1 and 2 of FIG. 6 during a SPECT scanning procedure along an elliptical trajectory.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and/or functional details disclosed herein are not to be interpreted as limiting the scope of the claims, but are merely provided as an example to teach one having ordinary skill in the art to make and use the invention.

Referring now to the Figures; FIG. 2 illustrates a known SPECT scanning system wherein each of a pair of detectors, 1 and 2, form a 90° angle with respect to one another. In the figure, it is seen that when a patient is centrally positioned between detectors 1 and 2, the patient's heart is not centered between detectors 1 and 2, but is offset such that distances $D_1$ and $D_2$ are not equal to one another. Thus, as shown in FIG. 3, as detectors 1 and 2 follow their elliptical trajectory about the patient to scan the heart, the distances $D_1$ and $D_2$ vary as the trajectory is traversed. Consequently, because the geometric efficiency of the detectors is dependent upon the distance of the detectors to the object, it is not maximized because the heart is offset.

As illustrated in FIGS. 1 and 4-7, the present invention addresses the above-identified SPECT scanning problems by providing a method wherein the starting angle of at least two SPECT detectors, is optimized based on a physical characteristic of an object to be scanned, e.g., the spatial location of the object within the radiation field of the SPECT scanning system, the distance between the detectors and the object, signal to noise ratio, etc.

Figure 1:
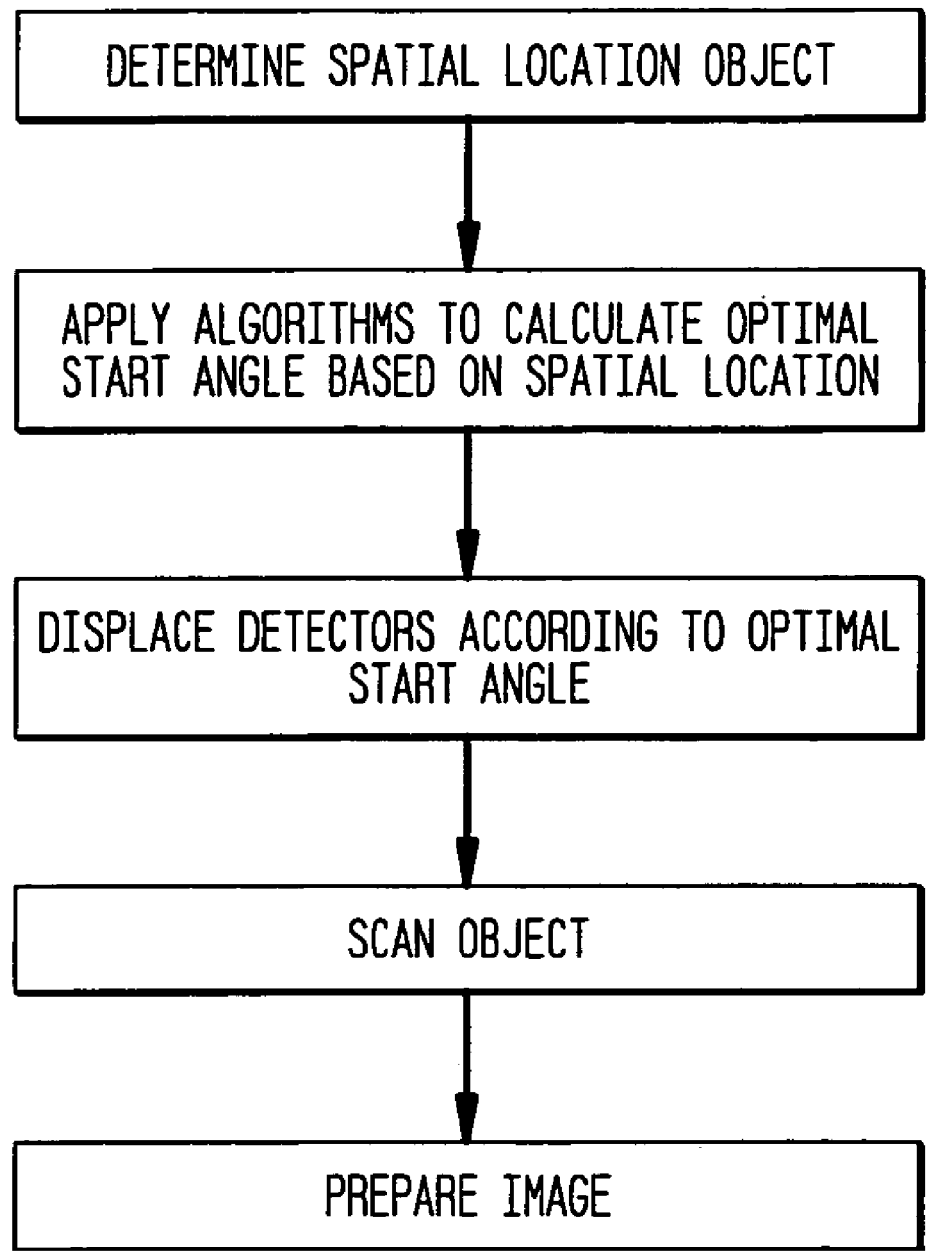
FIG. 1 is a flow diagram illustrating a method according to the present invention.

As illustrated in FIG. 1, an exemplary embodiment the invention broadly comprises the steps of determining a spatial location of an object within a radiation field, calculating an optimal starting angle of at least two detectors based on the spatial location of the object such that the geometrical efficiency of the detectors along a trajectory can be maximized, angularly displacing the detectors based on the calculated optimal starting angle, scanning the object within the field to detect one or more gamma photons emanating from the object, and preparing an image from the one or more detected gamma photons.

According to the method, the spatial position of the object can be determined using a preliminary image of the object to be scanned, for example, by using an attenuation (μ) map of a patient. Alternatively, the spatial position of the object can be estimated using known pre-existing data regarding a patient or information pertaining to typical circumstances, e.g., average positional location of the human heart in typical subjects. Once the spatial position of the object is known, the distance between the object and the detectors can be determined to determine the optimal starting angle.

Calculation of the optimal starting angle is based on the fact that the number of counts detected by a detector is inversely proportional to the square of the distance from the source of gamma photons to a detector (1). Consequently, a summation of the square of the distances from the object to a detector can provide an estimate of the count rate and a distance function can be described for a pair of detectors by:

$$D(\phi)=D_1^2(\phi)+D_2^2(\phi) \quad (1)$$

wherein $\phi$ is the detector rotation angle during a scan. During a scan period $\theta$, the geometric efficiency of the detectors can be maximized if along the trajectory an objective function described by equation (2) achieves a minimum:

$$f(\alpha) = \int_\alpha^{\alpha+\theta} D(\varphi)d\varphi \quad (2)$$

where $\alpha$ is the starting angle of the detectors.

Using the minimum a calculated, the starting angle of the detector assembly can, thus, be modified such that the scan time can be reduced while a like number of counts acquired.

The above-described algorithms, or other algorithms, for optimizing the start angle of the detectors, can be in the form of a software application input into the electronics of the SPECT scanning system. The spatial location of the object to be scanned can be automatically determined using the preliminary image data, any preexisting data, or estimates. The optimal starting angle can be automatically calculated based on the spatial location of the object and the angular disposition of the detectors with respect to one another. The detectors can then be automatically adjusted based on the calculation. Thereafter, the object may be scanned and an image prepared therefrom as is known.

Figure 4:
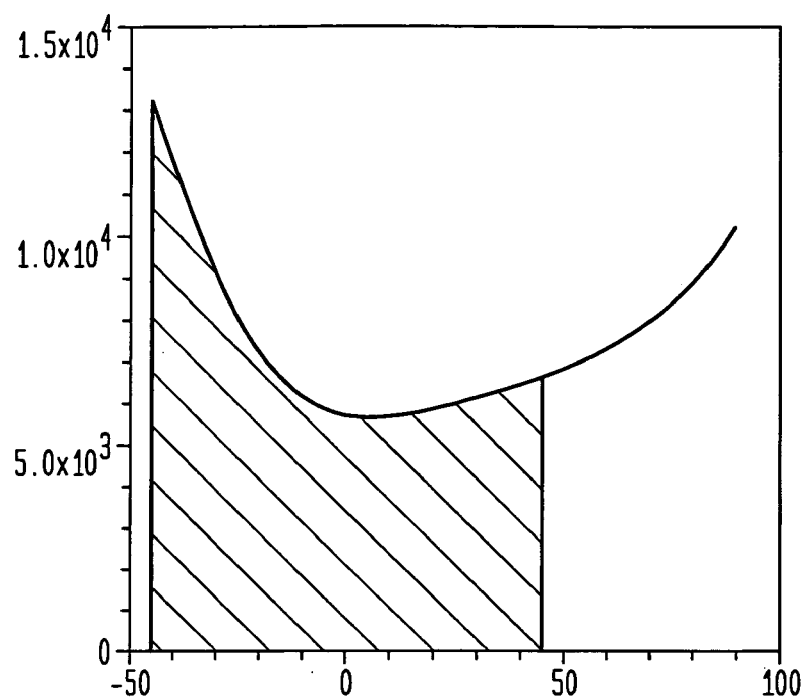
FIG. 4 illustrates a graph of a distance function, $D(\phi)=D_1^2(\phi)+D_2^2(\phi)$, along a scan trajectory from −45° to 90°; the shaded region illustrates the distance function from −45° to 45°.

FIG. 4 is a graphical representation of the distance function, $D(\phi)$, for a pair of detectors disposed at 90° with respect to one another wherein the scan period range is from −45° to 90°. In the figure, the scan period range from −45° to 45° is marked with shaded lines. As can be seen, the area under the curve, that is, the distance from the detectors to the object, is smaller where the starting angle is larger than −45° but smaller than 0°. Consequently, the geometric efficiency of the detectors can be increased by modifying the start angle of the detectors to an angle between −45° and 0°.

Figure 5:
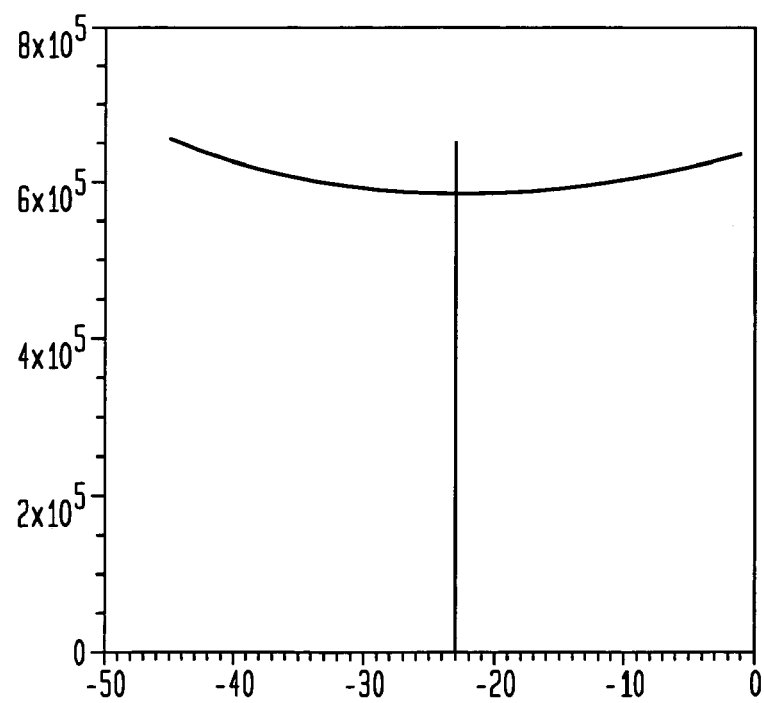
FIG. 5 illustrates an objective function, $$f(\alpha) = \int_\alpha^{\alpha+\theta^\circ} D(\varphi)d\varphi,$$

FIG. 5 is a graphical representation illustrating the objective function change, $$f(\alpha) = \int_{\alpha}^{\alpha+90°} D(\varphi)d\varphi,$$

for a pair of detectors disposed at 90° with respect to one another. As shown in the figure, when the starting angle of the detectors is modified between −45° and 0°, the minimum of the objective function is achieved at −23°. Thus, based on the objective function, a starting angle of −23° optimizes the geographic efficiency of the detectors along the trajectory. When compared with starting angles of known SPECT scanning devices, typically −45°, a −23° starting angle provides approximately 9% more counts over a 90° scan period. Consequently, where the −23° starting angle is utilized, the scan time is reduced while simultaneously acquiring the same number of counts.

Similarly, as illustrated in FIGS. 6 and 7, when the starting angle of detectors 1 and 2 is modified according to the present invention to an angle of approximately −23°, distances $D_1$ and $D_2$ are shorter when compared with distances $D_1$ and $D_2$ at starting angle of −45°. Similarly, throughout several portions of the scan period, it is seen that the distances of $D_1$ and $D_2$ at a −23° starting angle are less than if the starting angle were −45°. Consequently, the geometric efficiency of the detectors is increased at a −23° starting angle such that a shorter scan time can be obtained.

Furthermore, if attenuation of a patient's tissue is taken into account, the affects of a modified starting angle according to the invention are more significant and favorable; attenuation of tissue exponentially reduces the number of counts due to increases in the gamma photon travel distance within body. In other words, disposing the detectors at the modified angle reduces the amount of tissue that the gamma photons must traverse and will increase the number of counts.

The experimental data, thus, illustrates that the scanning method according to the present invention can reduce SPECT scanning times by approximately 9% when compared with current procedures. Calculating and modifying the starting angle of detectors, to an optimal angular position based on the spatial location of the object, allows the detectors to travel optimally along a scanning trajectory to receive a required number of counts in less time. In sum, shorter scanning times can serve to reduce stress that a patient may incur and render a patient more conducive to undergoing SPECT procedures. Additionally, reductions in scanning time increase image quality as reduced scanning times decrease the likelihood of patient movement during scanning procedures. Furthermore, when the geometric efficiency of the detectors is optimized along a trajectory, the difference in the number of counts between each detector can be reduced, which can improve image reconstruction when using filtered back projection.

It should be appreciated by those having skill in the art that while the exemplary embodiment described herein describes a pair of detectors angularly disposed with respect to one another at an angle of 90°, the angular disposition of the detectors with respect to one another may vary. For example, the detectors may be disposed at angles of 76°, 180°, etc. Also, while the trajectory of the detectors of the exemplary embodiment is described as being elliptical, the present method may be applied to optimize the geometric efficiency of detectors along any trajectory. Furthermore, while the scan period of the exemplary embodiment is described as 90°, the scan period is not so restricted. Also, while the present invention has been described in association with optimizing geometric efficiencies of detectors based on spatial location, geometric efficiencies of the detectors can be optimized on the basis of other physical characteristics of an object, for example, signal to noise ratio, shape of an object, etc.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method of acquiring images from a radiation field comprising:
   determining a spatial location of an object within the field;
   calculating an optimal scan starting angle, with respect to said object, of a configuration of at least two detectors angularly disposed with respect to each other at a preselected angle, based on the spatial location of the object such that the geometrical efficiency of the configuration of detectors along a trajectory can be maximized;
   angularly displacing the configuration of detectors with respect to said object, based on the calculated optimal scan starting angle;
   scanning the object within the field with said configuration of detectors starting at said optimal scan starting angle to detect one or more gamma photons emanating from the object; and,
   preparing an image from the one or more detected gamma photons.

2. The method of claim 1 wherein the configuration of detectors comprises a pair of detectors configured for performing SPECT.

3. The method of claim 2 wherein the optimal scan starting angle of the pair of detectors can be described by:

$$D(\varphi) = D_1^2(\varphi) + D_2^2(\varphi); \text{ and,}$$

$$f(\alpha) = \int_{\alpha}^{\alpha+\theta°} D(\varphi)d\varphi$$

wherein,
   D corresponds to detector distance from the object;
   θ corresponds to a period of the trajectory;
   φ corresponds to detector angle during scanning; and,
   α corresponds to detector starting angle; and,
   f(α) achieves a minimum value.

4. The method of claim 3 wherein θ is 90°.

5. The method of claim 4 wherein the pair of detectors is disposed at a 90° angle with respect to each other.

6. The method of claim 3 wherein θ is 180°.

7. The method of claim 6 wherein the pair of detectors is disposed at a 180° angle with respect to each other.

8. The method of claim 3 wherein the pair of detectors is disposed at a 76° angle with respect to each other.

9. The method of claim 3 wherein the trajectory comprises an arcuate portion.

10. The method of claim 3 wherein the trajectory comprises a line portion.

11. A method of acquiring images from a radiation field comprising:
   determining a physical characteristic of an object within the field;
   calculating an optimal scan starting angle, with respect to said object, of a configuration of at least two detectors angularly disposed with respect to each other at a preselected angle, based on the physical characteristic of the object and a trajectory of the configuration of at least two detectors such that the geometric efficiency of the configuration of detectors along the trajectory can be maximized;
   angularly displacing the configuration of detectors with respect to said object, based on the calculated optimal scan_starting angle;
   scanning the object with said configuration of detectors starting at said optimal scan starting angle within the field to detect one or more gamma photons emanating from the object; and,
   preparing an image from the one or more detected gamma photons.

12. The method of claim 11 wherein the physical characteristic is spatial location of the object within the field.

13. The method of claim 12 wherein the configuration of detectors comprises a pair of detectors configured for performing SPECT.

14. The method of claim 13 wherein the optimal scan starting angle of the pair of detectors can be described by:

$$D(\varphi) = D_1^2(\varphi) + D_2^2(\varphi); \text{ and,}$$

$$f(\alpha) = \int_\alpha^{\alpha+\theta} D(\varphi) d\varphi$$

wherein,
   B corresponds to detector distance from the object;
   θ corresponds to period of the trajectory;
   φ corresponds to detector angle during scanning; and,
   α corresponds to detector starting angle; and,
   f(α) achieves a minimum value.

15. The method of claim 14 wherein θ is 90°.

16. The method of claim 15 wherein the pair of detectors are disposed at a 90° angle with respect to one another.

17. The method of claim 14 wherein θ is 180°.

18. The method of claim 17 wherein the pair of detectors are disposed at a 180° angle with respect to one another.

19. The method of claim 14 wherein the pair of detectors are disposed at a 76° angle with respect to one another.

20. The method of claim 14 wherein the trajectory comprises an arcuate portion.

21. The method of claim 14 wherein the trajectory comprises a line portion.

22. The method of claim 11 wherein the physical characteristic is signal to noise ratio.

23. A method of acquiring images with a SPECT scanning system comprising:
   determining a spatial location of an object to be scanned;
   calculating an optimal rotational scan starting angle of a configuration of at least two detectors angularly disposed with respect to each other at a preselected angle, based on the spatial location of the object and the trajectory of the configuration of at least two detectors such that the geometrical efficiency of the detectors can be maximized along the trajectory;
   rotationally displacing the configuration of detectors based on the calculated optimal rotational scan starting angle;
   scanning the object with said configuration of detectors starting at said optimal rotational scan starting angle within the field to detect one or more gamma photons emanating from the object; and, preparing an image from the one or more detected gamma photons.

* * * * *